US010548609B2

(12) United States Patent
Ramsey et al.

(10) Patent No.: US 10,548,609 B2
(45) Date of Patent: Feb. 4, 2020

(54) SURGICAL LIGATION CLIP

(71) Applicant: TELEFLEX MEDICAL INCORPORATED, Morrisville, NC (US)

(72) Inventors: Michael Dell Ramsey, Raleigh, NC (US); David Lee Foshee, Apex, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 238 days.

(21) Appl. No.: 15/668,170

(22) Filed: Aug. 3, 2017

(65) Prior Publication Data

US 2018/0036008 A1 Feb. 8, 2018

Related U.S. Application Data

(60) Provisional application No. 62/370,502, filed on Aug. 3, 2016.

(51) Int. Cl.
| *A61B 17/122* | (2006.01) |
| *A61B 17/08* | (2006.01) |
| *A61B 17/00* | (2006.01) |

(52) U.S. Cl.
CPC .......... *A61B 17/122* (2013.01); *A61B 17/083* (2013.01); *A61B 2017/00588* (2013.01); *A61B 2017/086* (2013.01)

(58) Field of Classification Search
CPC ....... A61B 17/083; A61B 17/08; A61B 17/12; A61B 17/122; A61B 17/42; A61B 17/1227; A44B 6/00; Y10T 24/44274; Y10T 24/44282; Y10T 24/00; Y10T 24/10; Y10T 24/13; A45D 8/00; A45D 8/06;
(Continued)

(56) References Cited

U.S. PATENT DOCUMENTS

| 1,728,322 A | 9/1929 | Max et al. |
| 3,503,397 A | 3/1970 | Raible et al. |

(Continued)

FOREIGN PATENT DOCUMENTS

| CN | 101543418 A | 9/2009 |
| CN | 105054989 A | 11/2015 |

(Continued)

*Primary Examiner* — George J Ulsh
(74) *Attorney, Agent, or Firm* — Baker & Hostetler LLP

(57) ABSTRACT

A surgical clip may be configured to ligate tissue. The surgical clip may include first and second leg members. The first leg member may have a proximal portion, a distal portion, a convex first inner surface, and a convex first outer surface. The first leg member may also include an inner portion at least partially defining the first inner surface and an outer portion at least partially defining the first outer surface. The inner and outer portions may be joined at first and second portions of the first leg member and separated by a channel. The second leg member may include a proximal portion, a distal portion, a second inner surface, and a second outer surface. The first and second leg members may be movable relative to each other between open and closed configurations, and the first and second inner surfaces may be configured to ligate the tissue when in the closed configuration.

29 Claims, 8 Drawing Sheets

(58) Field of Classification Search
CPC ... A45D 8/12; A45D 8/16; A45D 8/20; A45D 8/22; A45D 8/24; A45D 8/26; A45D 8/32
USPC .......................... 606/157; 132/48, 276–279
See application file for complete search history.

(56) References Cited

U.S. PATENT DOCUMENTS

| | | |
|---|---|---|
| 3,766,925 A | 10/1973 | Rubricius |
| 3,825,012 A | 7/1974 | Nicoll |
| 3,867,944 A | 2/1975 | Samuels |
| 3,874,042 A | 4/1975 | Eddleman et al. |
| 4,337,774 A | 7/1982 | Perlin |
| 4,345,600 A | 8/1982 | Rothfuss |
| 4,346,869 A | 8/1982 | MacNeill |
| 4,390,019 A | 6/1983 | LeVeen et al. |
| 4,418,694 A | 12/1983 | Beroff et al. |
| 4,450,840 A | 5/1984 | Mericle et al. |
| 4,458,682 A | 7/1984 | Cerwin |
| 4,476,865 A | 10/1984 | Failla et al. |
| 4,487,205 A | 12/1984 | Di Giovanni et al. |
| 4,519,392 A | 5/1985 | Lingua |
| 4,527,562 A | 7/1985 | Mericle |
| 4,550,729 A | 11/1985 | Cerwin et al. |
| 4,579,118 A | 4/1986 | Failla |
| 4,588,160 A | 5/1986 | Flynn et al. |
| 4,589,626 A | 5/1986 | Kurtz et al. |
| 4,638,804 A | 1/1987 | Jewusiak |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,096 A | 5/1989 | Oh et al. |
| 4,870,965 A | 10/1989 | Jahanger |
| 4,936,447 A | 6/1990 | Peiffer |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,160,339 A | 11/1992 | Chen et al. |
| 5,171,251 A | 12/1992 | Bregen et al. |
| 5,171,252 A | 12/1992 | Friedland |
| 5,201,416 A | 4/1993 | Taylor |
| 5,234,449 A | 8/1993 | Bruker et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,462,555 A | 10/1995 | Bolanos et al. |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,575,802 A | 11/1996 | McQuilkin et al. |
| 5,667,516 A | 9/1997 | Allen |
| 5,697,938 A | 12/1997 | Jensen et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,810,853 A | 9/1998 | Yoon |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,997,548 A | 12/1999 | Jahanger |
| 6,015,417 A | 1/2000 | Reynolds, Jr. |
| 6,131,576 A | 10/2000 | Davis |
| 6,210,419 B1 | 4/2001 | Mayenberger et al. |
| 6,217,590 B1 | 4/2001 | Levinson |
| 6,261,303 B1 | 7/2001 | Mayenberger et al. |
| 6,349,727 B1 | 2/2002 | Stewart, Jr. |
| 6,391,035 B1 | 5/2002 | Appleby et al. |
| 6,419,682 B1 | 7/2002 | Appleby et al. |
| 6,537,289 B1 | 3/2003 | Kayan et al. |
| 6,699,258 B1 | 3/2004 | Sadler et al. |
| 6,719,766 B1 | 4/2004 | Buelna et al. |
| 6,824,547 B2 | 11/2004 | Wilson, Jr. et al. |
| 6,843,253 B2 | 1/2005 | Parkes |
| 6,863,675 B2 | 3/2005 | Wilson, Jr. |
| 6,880,699 B2 | 4/2005 | Gallagher |
| 6,989,017 B2 | 1/2006 | Howell et al. |
| 7,001,412 B2 | 2/2006 | Gallagher et al. |
| 7,052,504 B2 | 5/2006 | Hughett |
| 7,131,977 B2 | 11/2006 | Fowler |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,402,164 B2 | 7/2008 | Watson, Jr. et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,262,639 B2 | 9/2012 | Mathias |
| 9,084,596 B2 | 7/2015 | Stanley et al. |
| 9,220,507 B1 | 12/2015 | Patel et al. |
| 9,445,820 B2 | 9/2016 | Whiting |
| 9,456,824 B2 | 10/2016 | Willett et al. |
| 9,855,053 B2 | 1/2018 | Bagaoisan et al. |
| 2002/0068946 A1 | 6/2002 | Kortenbach et al. |
| 2002/0111640 A1 | 8/2002 | Krause et al. |
| 2002/0169459 A1 | 11/2002 | Porat |
| 2003/0074009 A1 | 4/2003 | Ramsey et al. |
| 2004/0059359 A1 | 3/2004 | Wilson, Jr. |
| 2004/0172043 A1 | 9/2004 | Watson, Jr. et al. |
| 2005/0149069 A1 | 7/2005 | Bertolero |
| 2005/0165421 A1 | 7/2005 | Wilson, Jr. et al. |
| 2005/0165422 A1 | 7/2005 | Wilson, Jr. |
| 2005/0165423 A1 | 7/2005 | Gallagher et al. |
| 2005/0165429 A1 | 7/2005 | Douglas et al. |
| 2006/0217749 A1 | 9/2006 | Wilson, Jr. et al. |
| 2007/0083218 A1 | 4/2007 | Morris |
| 2007/0118161 A1 | 5/2007 | Kennedy et al. |
| 2007/0149989 A1 | 6/2007 | Santilli et al. |
| 2007/0276417 A1 | 11/2007 | Mendes, Jr. et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0088783 A1 | 4/2009 | Kennedy et al. |
| 2009/0171380 A1 | 7/2009 | Whiting |
| 2009/0240266 A1 | 9/2009 | Dennis |
| 2010/0114131 A1 | 5/2010 | Rotunda |
| 2010/0211080 A1 | 8/2010 | Trivisani et al. |
| 2010/0274268 A1 | 10/2010 | Singh et al. |
| 2011/0022079 A1 | 1/2011 | Miles et al. |
| 2011/0245848 A1 | 10/2011 | Rosenberg et al. |
| 2011/0295291 A1 | 12/2011 | Trivisani |
| 2012/0083803 A1 | 4/2012 | Atel et al. |
| 2013/0006271 A1 | 1/2013 | Vold et al. |
| 2013/0261642 A1 | 10/2013 | Willet et al. |
| 2014/0058411 A1 | 2/2014 | Soutorine et al. |
| 2014/0243862 A1 | 8/2014 | Bagaoisan et al. |
| 2016/0174981 A1* | 6/2016 | Fago ............... A61B 17/1227 606/157 |

(56) References Cited

U.S. PATENT DOCUMENTS

2016/0354089 A1 12/2016 Whiting
2018/0168659 A1 6/2018 Bagaoisan et al.

FOREIGN PATENT DOCUMENTS

| EP | 0086640 A2 | 8/1983 |
| EP | 0314064 A2 | 5/1989 |
| EP | 0201344 B1 | 12/1989 |
| EP | 1233705 B1 | 1/2008 |
| EP | 2074954 B1 | 8/2011 |
| GB | 2069848 A | 9/1981 |
| GB | 2 353 710 A | 3/2001 |
| GB | 2465560 A | 5/2010 |
| JP | 56-151034 A | 11/1981 |
| JP | 61-259652 A | 11/1986 |
| JP | 3-178648 A | 8/1991 |
| JP | 2002-345828 A | 12/2002 |
| WO | 2006/102578 A1 | 9/2006 |
| WO | 2012/075532 A1 | 6/2012 |

\* cited by examiner

SURGICAL LIGATION CLIP

PRIORITY

The present disclosure claims priority to U.S. Provisional Patent Application No. 62/370,502, filed on Aug. 3, 2016, the entire disclosure of which is incorporated by reference herein.

TECHNICAL FIELD

The present disclosure relates generally to medical devices, and more particularly, to surgical clips for ligation of tissue.

BACKGROUND

The ligation of tissue (e.g., blood vessels, lymph nodes, nerves, fallopian tubes, or cardiac tissue) is a common practice of many surgical procedures. For example, ligating blood vessels (e.g., veins or arteries) is often required during the resection of the blood vessels, for example, to remove an aneurysm. Ligation of tissue may be performed by closing the vessel with a ligation clip, or by suturing the vessel with surgical thread. The use of surgical thread for ligation requires complex manipulations of the needle and suture material to form the knots required to secure the vessel. Such complex manipulations are time consuming and difficult to perform, particularly in endoscopic surgical procedures, which are characterized by limited space and visibility. By contrast, ligation clips are relatively easy and quick to apply. Accordingly, the use of ligation clips in endoscopic as well as open surgical procedures has grown dramatically.

OVERVIEW

The present inventors recognize that there is a need to improve one more features of the ligation clips, such as initial retention of the tissue and pressure distribution. For example, current ligation clips are often subject to an undesired "watermelon-seeding" effect, when the tissue slips out of the ligation clip as it is closes. This effect may unfortunately result in tissue damage, a longer surgical procedure, and the surgeon applying excessive force to the tissue to ensure retention. Furthermore, after being closed on the tissue, the current ligation clips often apply a non-uniform pressure distribution. For example, the leg members of the current ligation clips are typically rigid and do not conform to tissue of different sizes, causing stress localization. The non-uniform pressure distribution may be especially problematic when the tissue is not properly positioned in the clip, for example, over-compression may occur when the tissue is positioned adjacent to either of a hinge portion or the latching mechanism. This non-uniform pressure distribution may result in tissue damage and/or rupture, especially when applied to overstressed., fibrotic, and/or infarcted tissue. Furthermore, the current ligation clips do not sufficiently ligate bundles of tissue, for example, due to varying sizes of the tissue in the bundle. The disclosed methods and systems are directed to mitigating or overcoming one or more of the problems set forth above and/or other problems in the prior art.

In one or more aspects, a surgical clip configured to ligate a tissue may include a first leg member and a second leg member. The first leg member may have a proximal portion, a distal portion, a convex first inner surface, and a convex first outer surface. The first leg member may also include an inner portion at least partially defining the first inner surface and an outer portion at least partially defining the first outer surface. The inner and outer portions may be joined at first and second portions of the first leg member and separated by a first channel. The second leg member may include a proximal portion, a distal portion, a second inner surface, and a second outer surface. The first and second leg members may be movable relative to each other between an open configuration and a closed configuration, and the first and second inner surfaces may be configured to ligate the tissue when in the closed configuration.

In some aspects, the first inner portion may be configured to be resiliently deflected in the closed configuration; the second inner surface may include a convex inner surface, and the first and second inner surfaces may be configured to pinch a proximal portion as the surgical clip is initially compressed; the first inner portion and the first outer portion may be integral to the first leg member; the first inner portion may have a width that may be substantially equal to a width of the first outer portion; the first channel may extend in a longitudinal direction for at least half of a length of the first leg member; the first channel may extend in the longitudinal direction for greater than three-quarters of the length of the first leg member; a hinge portion may join the proximal end portions of the first and second leg members; the hinge portion may be integral to the first and second leg members; the surgical clip may further include: at least one first tooth positioned on the first inner surface; and at least one second tooth positioned on the second inner surface; the first and second leg members may include latching elements configured to secure the surgical clip in the closed configuration; each of the first and second leg members may include at least one boss; the second leg member may include a second inner portion at least partially defining the second inner surface and a second outer portion at least partially defining the second outer surface, the second inner portion and the second outer portion may be joined at first and second portions of the second leg member and separated by a second channel defined between said second inner portion and said second outer portion of the second leg member; the second inner portion may include a convex inner surface, and the second outer portion may include a convex outer surface; and the second inner portion may include a concave outer surface, and the second outer portion may include a concave inner surface.

In one or more aspects, a method may include ligating a tissue with a surgical clip having a first leg member and a second leg member. The first leg member may include an inner portion, an outer portion, and a channel between the inner portion and the outer portion. The method may include moving the first leg member relative to the second leg member from an open configuration toward a closed configuration. The method may also include compressing at least a portion of the tissue between the first leg member and the second leg member by engaging the tissue with a convex inner surface of the inner portion. The method may further include deflecting the inner portion into the channel as the tissue is compressed.

In some aspects, resiliently deflecting the inner portion may include resiliently deflecting the inner portion toward a concave surface of an outer portion of the first leg member; the method may further include retracting the tissue with the surgical clip after compressing the at least a portion of the tissue; and moving the surgical clip into the closed configuration after retracting the tissue with the surgical clip; the method may further include securing the surgical clip in the closed configuration with latching elements on the first and second leg members.

In one or more aspects, a surgical clip configured to ligate a tissue may include a first leg member and a second leg member, and the first leg member may have an inner portion having a convex inner surface, an outer portion, and a channel between the inner portion and the outer portion. The first leg member may be configured to move relative to the second leg member from an open configuration toward a closed configuration, the first leg member and the second leg member may be configured to compress at least a portion of the tissue by engaging the tissue with the convex inner surface, and the inner portion may be configured to resiliently deflect into the channel as the tissue is compressed.

BRIEF DESCRIPTION OF THE DRAWINGS

In order that the disclosure may be readily understood, aspects of this disclosure are illustrated by way of examples in the accompanying drawings.

The same reference numbers are used in the drawings and the following detailed description to refer to the same or similar parts.

DETAILED DESCRIPTION

Figure 1:
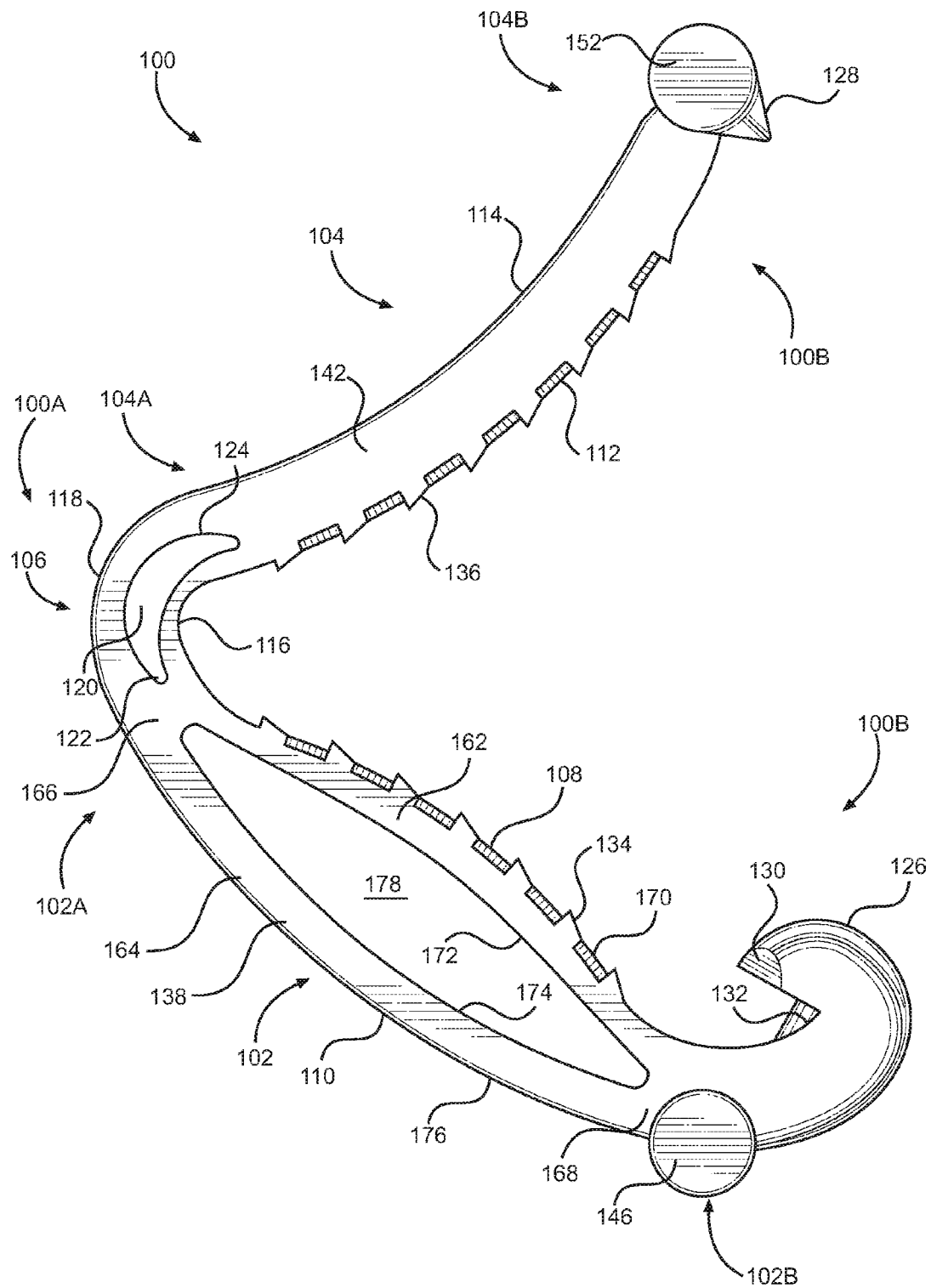
FIG. 1 illustrates a side elevation view of a first exemplary embodiment of a surgical ligation clip of the present disclosure.

The invention will now be described with reference to the figures, in which like reference numerals refer to like parts throughout, in accordance with conventional practice, as used herein, and unless otherwise indicated herein, the term "proximal end portion" refers to the specified end portion of a device or its component which is generally closer to the medical personnel handling or manipulating the device as it is intended to be used, and the term "distal end portion" shall refer to the specified end portion of a device or its component which is opposite the proximal end portion.

The present invention is generally directed to a surgical ligation clip configured to ligate tissue (e.g., a blood vessel). The clip may comprise first and second leg members configured to provide increased initial retention and pressure distribution. For example, the first leg member may comprise an inner portion (e.g, an inner rib) having a convex portion that enables pinching of a proximal portion of the tissue against a convex surface of the second leg member as the clip is initially compressed. In some embodiments, the pinching of the tissue may grasp the tissue to enable manipulation of the tissue as the clip is partially open. The convex surfaces may further include teeth that grasp and pull the tissue toward a proximal end portion of the clip, as the tissue is further compressed. The inner portion may be resiliently compressed toward a concave inner surface of an outer portion (e.g., an outer rib) of the first leg member providing favorable pressure distribution on the tissue as it is ligated. The flexibility of the inner portion may enable favorable pressure distribution on tissue of different shapes, sizes, and/or stiffnesses, and tissue compressed at different positions along the length of the clip. This may reduce leakage, tissue damage and/or rupture during the ligation, for example, of overstressed, fibrotic, and/or infarcted tissue, Furthermore, the flexibility of the inner portion may enhance ligation of a bundle of tissues, such as a plurality of lymph nodes. The flexibility of the inner portion may conform to the various tissues in the bundle, while ensuring sufficient pressure is applied to ligate each of the tissues in the bundle.

Figure 2:
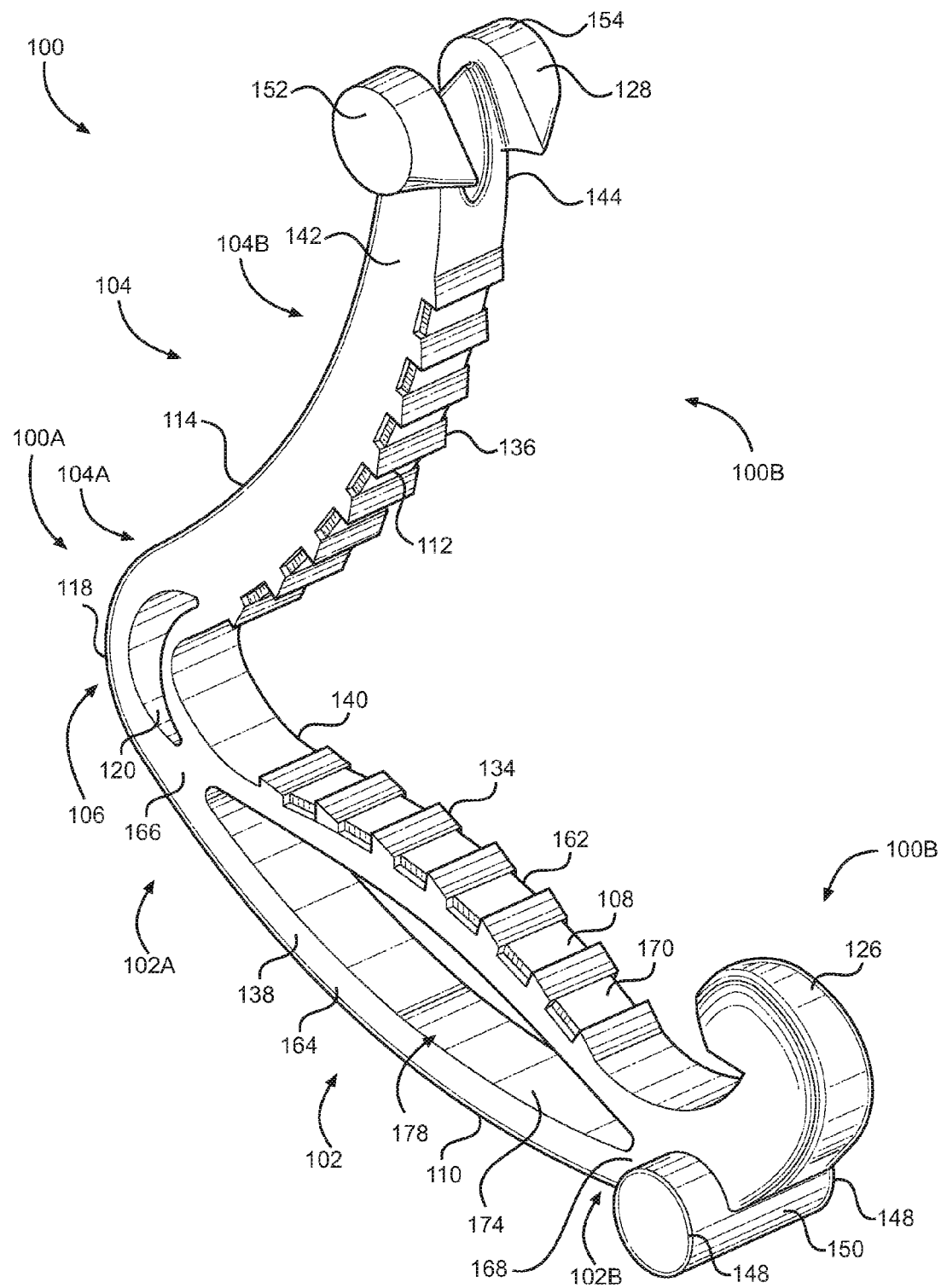
FIG. 2 illustrates a perspective view of the first embodiment of the surgical ligation clip of FIG. 1.
Figure 3:
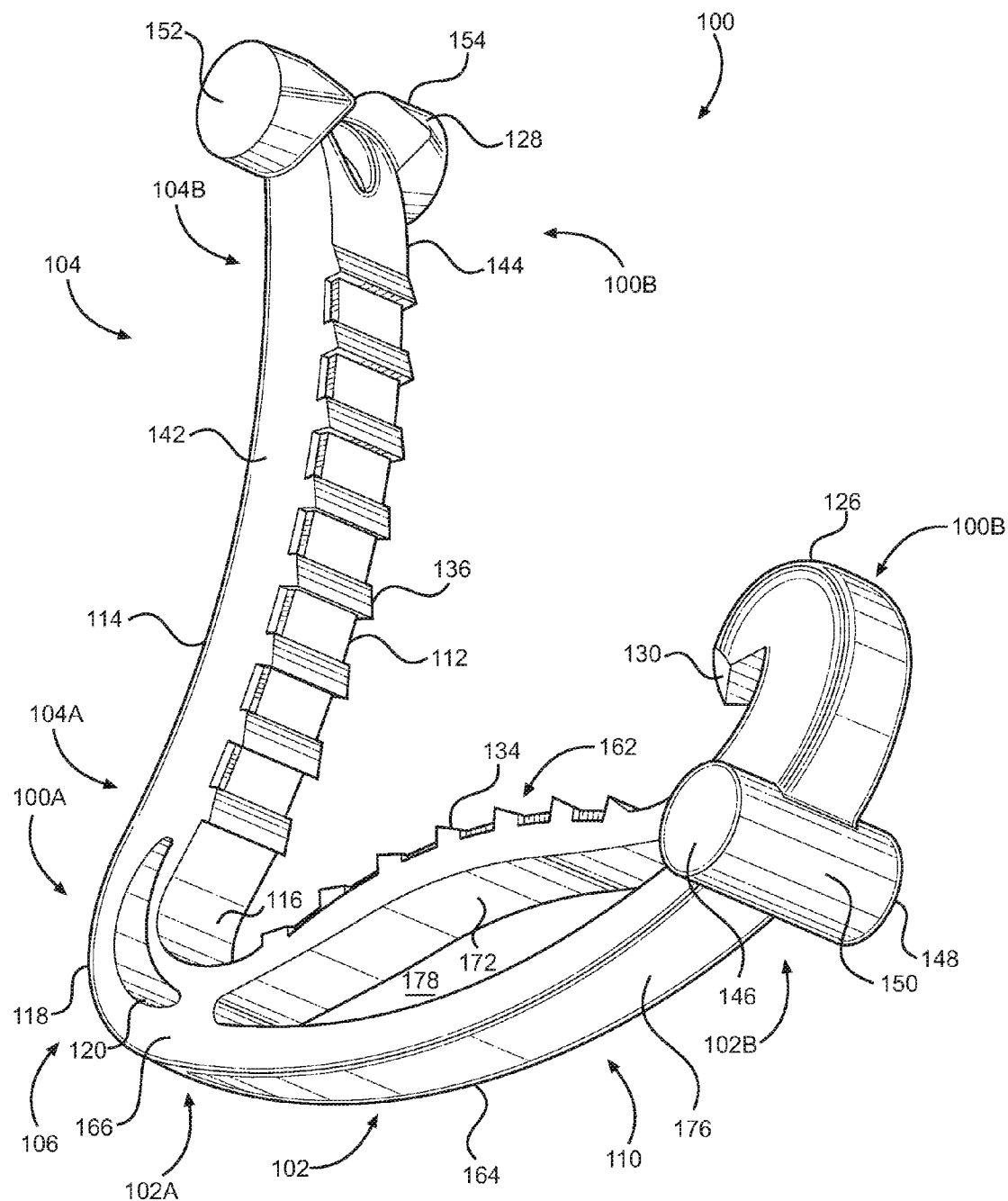
FIG. 3 illustrates another perspective view of the first exemplary embodiment of the surgical ligation clip of FIGS. 1 and 2.

FIG. 1 is a side elevation view of a first embodiment of a surgical ligation clip 100. FIGS. 2 and 3 show perspective views of clip 100. Clip 100 is particularly useful as hemostatic clips that can be latched around a vessel to thereby stop or reduce the flow of fluid through the vessel.

Clip 100 may have a proximal end portion 100A and a distal end portion 100B. Clip 100 may further include a first leg member 102 having a proximal end portion 102A and distal end portion 102B, and a second leg member 104 having a proximal end portion 104A and distal end portion 104B. First and second leg members 102, 104 may include surfaces having curved portions. For example, first leg member 102 may include a first inner surface 108 and a first outer surface 110, and second leg member 104 may include a second inner surface 112 and a second outer surface 114. As shown in FIG. 1, first inner surface 108 may include a convex portion, and first outer surface 110 may include a convex portion. Second inner surface 112 may include a convex portion, and second outer surface 114 may include a concave portion. First inner surface 108 and second inner surface 112 may be configured to pinch a proximal portion of the tissue as clip 100 is initially applied, and first inner surface 108 may be resiliently flexible along its length to distribute pressure over a width of the tissue as the tissue is ligated.

First and second leg members 102, 104 may be joined at proximal end portions 102A, 104A by a hinge portion 106. Hinge portion 106 may be resilient and/or integral to clip 100. Hinge portion 106 may have a continuous concave inner surface 116 and a continuous convex outer surface 118. Concave inner surface 116 of hinge portion 106 may join first inner surface 108 of first leg member 102 and second inner surface 112 of second leg member 104. Convex outer surface 118 of hinge portion 106 may join first outer surface 110 of first leg member 102 and second outer surface 114 of second leg member 104. Hinge portion 106 may also include a curved slot 120 located between curved hinge surfaces 116, 118, and may be positioned closer to concave inner surface 116 than to convex outer surface 118. Curved slot 120 may extend completely through hinge portion 106 from side to side and its opposite ends 122, 124 may extend into proximal end portions 102A, 102B of first and second leg members 102, 104, respectively. Curved slot 120 may provide added flexibility and resiliency to hinge portion 106, but concave inner surface 116 may prevent any portion of a clamped vessel from being trapped within curved slot 120.

Clip 100 may also include a latching mechanism formed by latching elements on first and second leg members 102, 104. For example, first leg member 102 may transition to a curved, C-shaped hook section 126 at its distal end. Second leg member 104 may transition to a pointed tip section 128 at its distal end. The distal portion of hook section 126 may curve inwardly and point generally toward concave inner surface 116 of hinge portion 106. Hook section 126 may have one or more transverse beveled surfaces 130 and a concave inner surface which merges with first inner surface 108 to define a latching member or recess 132. Latching recess 132 may conform and engage with tip section 128 in the course of compressing clip 100 into a latched or secured position around a vessel or other tissue.

Leg members 102, 104 may include one or more bosses along their length to engage a clip applier. For example, first leg member 102 may include cylindrical bosses 146, 148 (depicted in FIGS. 2-3) protruding perpendicular to each of opposed side surfaces 138, 140 adjacent to distal end portion 102B of first leg member 102 and immediately inward of hook section 126. In the illustrated example of clip 100, a bridge section 150 may couple bosses 146, 148 together, and bosses 146, 148 may project outwardly beyond first outer surface 110 of first leg member 102. Second leg member 104 may also include cylindrical bosses 152, 154 at distal end portion 104B, protruding perpendicular to each of opposed side surfaces 142, 144 of second leg member 104 and extending longitudinally forward beyond the point of tip section 128. In the practice of ligating a vessel, clip 100 may be designed to be compressed into a latched or locked position around the vessel through the use of an appropriate clip applier, such as a type described in U.S. Pat. No. 5,100,416, the entire disclosure of which is incorporated herein. The clip applier may engage and pivot bosses 146, 148, 152, 154 of clip 100 inwardly about hinge portion 106.

First leg member 102 may include an inner portion 162 and an outer portion 164 joined at a first portion 166 and a second portion 168 of first leg member 102. Inner portion 162 may include a convex portion When viewed from the inner side of first leg member 102, having an inner surface 170 that may be convex and an outer surface 172 that may be concave. Outer portion 164 may include a concave portion when viewed from the inner side of first leg member 102, having an inner surface 174 that may be concave and an outer surface 176 that may be convex. It is contemplated that inner portion 162 and/or outer portion 164 may have a number of different curvatures. For example, inner portion 162 may include one or more concave, convex, and/or flat inner surfaces and one or more concave, convex, and/or flat outer surfaces. Outer portion 164 may include one or more c concave, convex, and/or flat inner surfaces and one or more concave, convex, and/or flat outer surfaces.

Inner surface 170 of inner portion 162 may define at least a portion of first inner surface 108, and outer surface 176 of outer portion 164 may define at least a portion of first outer surface 110 of clip 100. For example, in some embodiments, inner portion 162 and outer portion 164 may extend greater than half of a length of first leg member 102 (e.g., defining greater than half of surfaces 108, 110). In some embodiments, inner portion 162 and outer portion 164 may extend greater than three-quarters of the length of first leg member 102 (e.g., defining greater than three-quarters of surfaces 108, 110). Each of inner portion 162 and outer portion 164 may have a thickness less than a thickness of second leg member 104. For example, the thickness of each of inner portion 162 and/or outer portion 164 may be substantially half of the thickness of each of first leg member 102 and second leg member 104. The reduced thickness of inner portion 162 may provide the desired flexibility to conform to tissue compressed by clip 100. Inner portion 162, outer portion 164, and second leg member 104 may have substantially the same width in the transverse direction.

Inner portion 162 and outer portion 164 may be separated by at least one aperture or channel 178 extending longitudinally along the clip 100 to enable compression of first leg member 102. The channel 178 may extend between side surfaces 138, 140 of first leg member 102. For example, channel 178 may enable inner portion 162 to resiliently compress toward outer portion 164 and distribute load along the length of the tissue, while more effectively gripping and retaining the tissue within clip 100. In some embodiments, the channel 178 may extend in a longitudinal direction more than half a length of first leg member 102. In some embodiments, the channel 178 may extend in a longitudinal direction greater than three-quarters of the length of first leg member 102, as depicted in FIG. 1. The concavity of outer portion 164 may provide additional room for resilient deflection of inner portion 162, allowing clip 100 to ligate and properly distribute pressure to tissue of varying shapes, sizes, and/or stiffnesses. For example, inner portion 162 may provide continuous ligating pressure to tissue in a latched configuration, even as the tissue necrotizes and shrinks. In some embodiments, one or more ribs may extend between inner portion 162 and outer portion 164 to provide stiffness to first leg member 102 when desired.

As further shown in the embodiment of FIGS. 1-3, clip 100 may include a first plurality of teeth 134 protruding on first inner surface 108, and a second plurality of teeth 136 protruding on second inner surface 112. Teeth 134, 136 may maximize security of compressed tissue and minimize migration. Teeth 134, 136 may extend the width of first and second leg members 102, 104, and may be angled towards proximal end portion 102A of clip 100. In some embodiments, teeth 134, 136 may aid in initial pinching and pulling of the tissue toward proximal end portion 100A, and retention or gripping of the tissue when further compressed or ligated. Teeth 134, 136 may also enable clip 100 to manipulate tissue when clip 100 is at least partially open. In some embodiments, teeth 134, 136 may be omitted. In some embodiments, one or more of teeth 134, 136 may be in an "out-board" configuration (e.g., extending from one or more of the side surfaces 136-142), as disclosed in U.S. Provisional Patent Application No. 62/523,562, the entire disclosure of which is incorporated. herein.

FIGS. 4A-D illustrate a series of configurations of clip 100 of FIG. 1 being applied to a tissue 500 (e.g., a blood vessel). One or more of the configurations shown in FIGS. 4A-D may provide one or more steps of a method of compressing and/or manipulating tissue 500 (e.g., temporarily or permanently ligating a blood vessel).

Figure 4A:
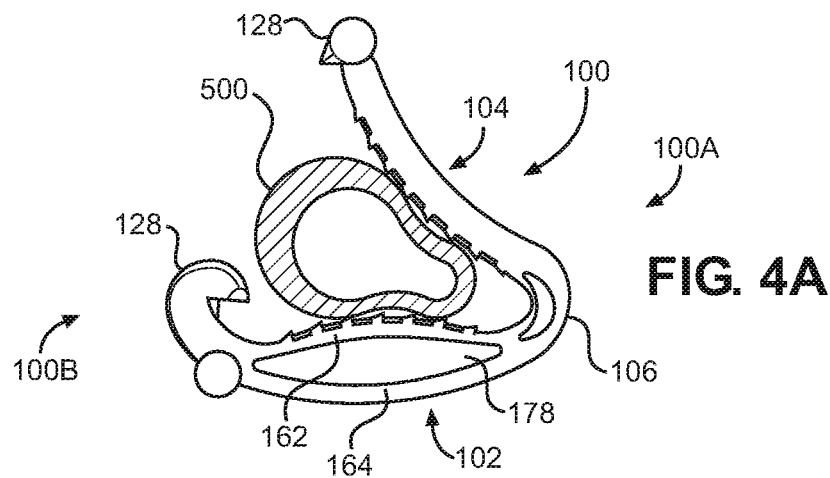
FIGS. 4A-D illustrate a series of configurations of the first exemplary embodiment of the surgical ligation clip of FIGS. 1-3, when applied to close or ligate tissue.
Figure 4B:
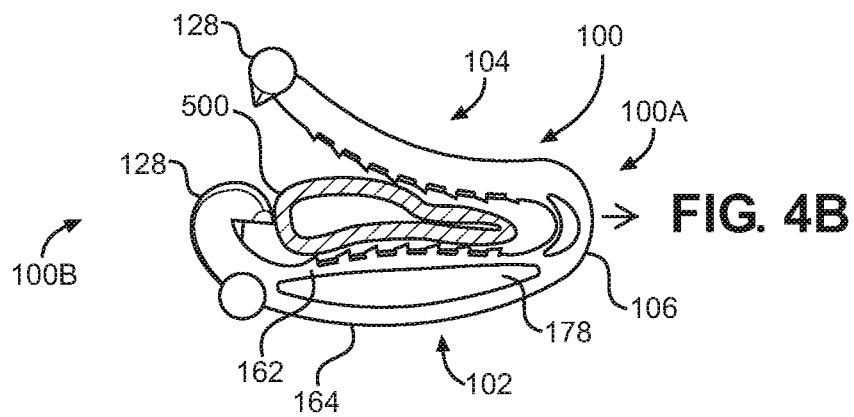

As shown in FIG. 4A, tissue 500 may be positioned between first and second leg members 102, 104 when clip 100 is in an open configuration. As further shown in FIG. 4B, clip 100 may be initially compressed to pinch a proximal portion of tissue 500 between inner surfaces 108, 112 proximate to hinge portion 106, preventing tissue 500 from sliding out of distal end portion 100B as clip 100 closes (e.g., a "watermelon-seeding" effect). The initial pinching of tissue 500 may also allow a surgeon to manipulate tissue 500 with clip 100 While being at least partially open, as exemplary depicted in FIG. 4B. For example, if tissue 500 is proximate to other bodily structures, the surgeon may pinch (or compress) and retract tissue 500 away from the other structures to prevent the other structures from interfering with the ligation and/or to prevent the latching mechanism from damaging the other structures. The initial pinching of tissue 500 may further aid in skeletonizing tissue 500 prior to closure.

Figure 4C:
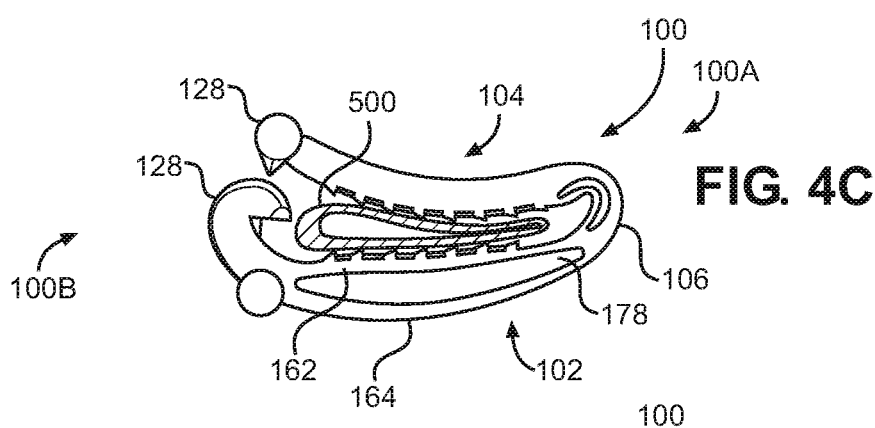
Figure 4D:
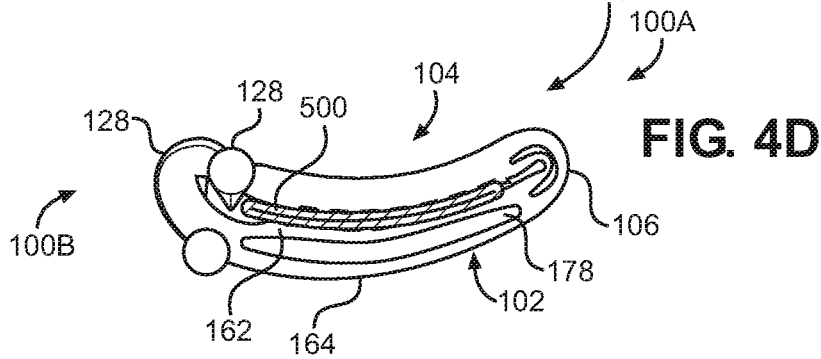

As shown in FIG. 4C, tissue 500 may be further compressed by first and second leg members 102, 104. In some embodiments, inner surfaces 108, 112 and teeth 134, 136 may further pinch and pull tissue 500 toward hinge portion 106. The pinching and pulling of tissue 500 may enhance security of tissue 500 and further reduce the potential of the "watermelon-seeding" effect. For example, second leg member 104 may pull tissue 500 in the proximal direction by sliding along inner surface 170 toward hinge portion 106, or vice versa. The proximal sliding of second leg member 104 may be provided by the interaction of the convexity of each of first inner surface 108 and second inner surface 112. For example, second inner surface 112 may contact (either directly or through tissue) a proximal portion of inner surface 170 of inner portion 162, which causes second leg member 104 and/or tissue 500 to slide proximally toward hinge portion 106. The proximal sliding of second leg member 104 may, additionally or alternatively, be provided by abutment of tip section 128 of first leg member 102 with hook section 126 of second leg member 104. For instance, the abutment of tip section 128 onto a proximal angled surface of hook section 126 may cause first leg member 102 to elongate relative to second leg member 104, and second leg member 104 to pull tissue 500 toward hinge portion 106. The compression of clip 100 may progressively ligate tissue 500 from proximal end portion 100A to distal end portion 100B of clip 100.

The compression of clip 100 may further resiliently deflect inner portion 162 toward outer portion 164 distributing the pressure along the width of tissue 500. For example, inner portion 162 may conform to the size of tissue 500, apply spring-like resilient pressure along the entire width of tissue 500, and/or reduce any potential stress localizations. Outer portion 164 may also elongate as clip 100 is compressed. As further shown in FIG. 4D, clip 100 may secure tissue 500 in a ligated configuration, for example, through the latching mechanism. Inner portion 162 may provide continuous ligating pressure to tissue 500 in the latched configuration, even as tissue 500 necrotizes and shrinks.

Figure 5A:
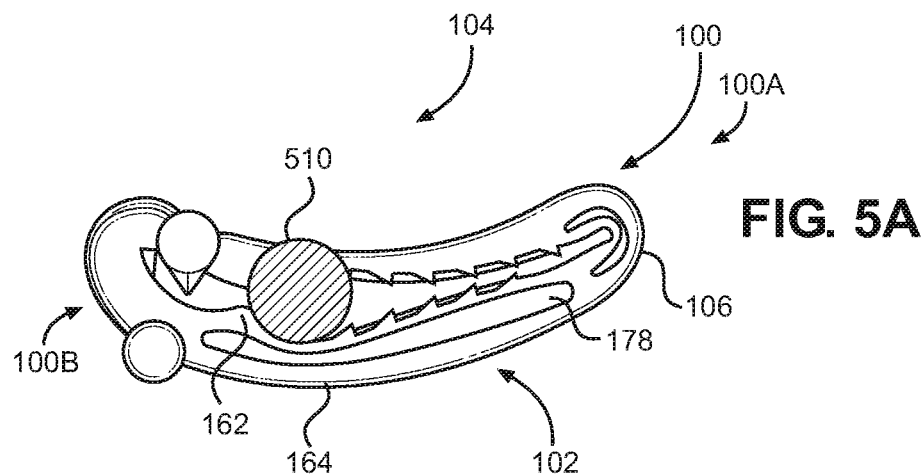
FIGS. 5A-B illustrate additional configurations of the first exemplary embodiment of the surgical ligation clip of FIGS. 1-3, when applied to close or ligate tissue.
Figure 5B:
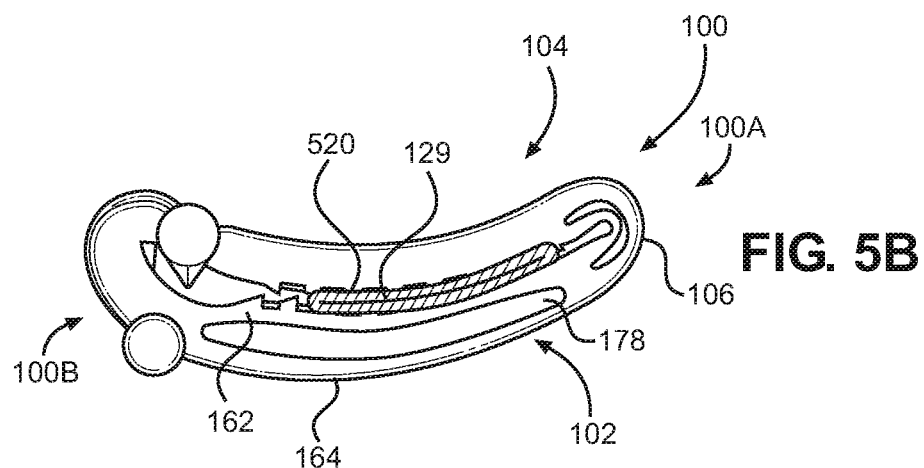

As further shown in FIGS. 5A-B, clip 100 may be configured to provide a favorable pressure distribution to different types and sizes of tissue, even when the tissue is not centered in clip 100. For example, clip 100 may ensure proper pressure distribution to substantially rigid tissue 510 (as depicted in FIG. 5A) or substantially compliant tissue 520 (as depicted in FIG. 5B). For example, tissue 510 may be overstressed, fibrotic, and/or infarcted tissue that may be subject to stress localization when compressed because of the inability to conform to compressive loads. Clip 100 may reduce any resulting stress localization of tissue 500 through deflection of inner portion 162. Inner portion 162 may resiliently deflect into channel 178, conform to tissue 510, 520, and prevent any over compression. When applied to compliant tissue 520, inner portion 162 may deflect a reduced extent. Furthermore, the flexibility of the inner portion may enhance ligation of a bundle of tissues, such as a plurality of lymph nodes. The flexibility of the inner portion may conform to the various tissues in the bundle, while ensuring sufficient pressure is applied to ligate each of the tissues in the bundle.

Inner portion 162 may also deflect along any portion of its length. For example if tissue 510, 520 is positioned proximate to hinge portion 106, a proximal portion of inner portion 162 may deflect to accommodate tissue 510, 520. On the other hand, if tissue 510, 520 is positioned proximate to the latching mechanism, a distal portion of inner portion 162 may deflect to accommodate tissue 510, 520. In that sense, clip 100 may reduce stress localization due to proximity of tissue 510, 520 to either of the latching mechanism or hinge portion 106.

Clip 100 may further be applied to tissue bundles (e.g., tissue, vessels, glands, lymph nodes, and nerves) having irregular shapes. For example, in ligating the dorsal venous complex (DVC) during a prostatectomy, it may be difficult to ensure each blood vessel is clamped. However, inner portion 162 may conform individually to each of the blood vessels of the DVC to ensure that adequate ligation pressure is applied to each blood vessel, tissue structure or lymph node.

Figure 6:
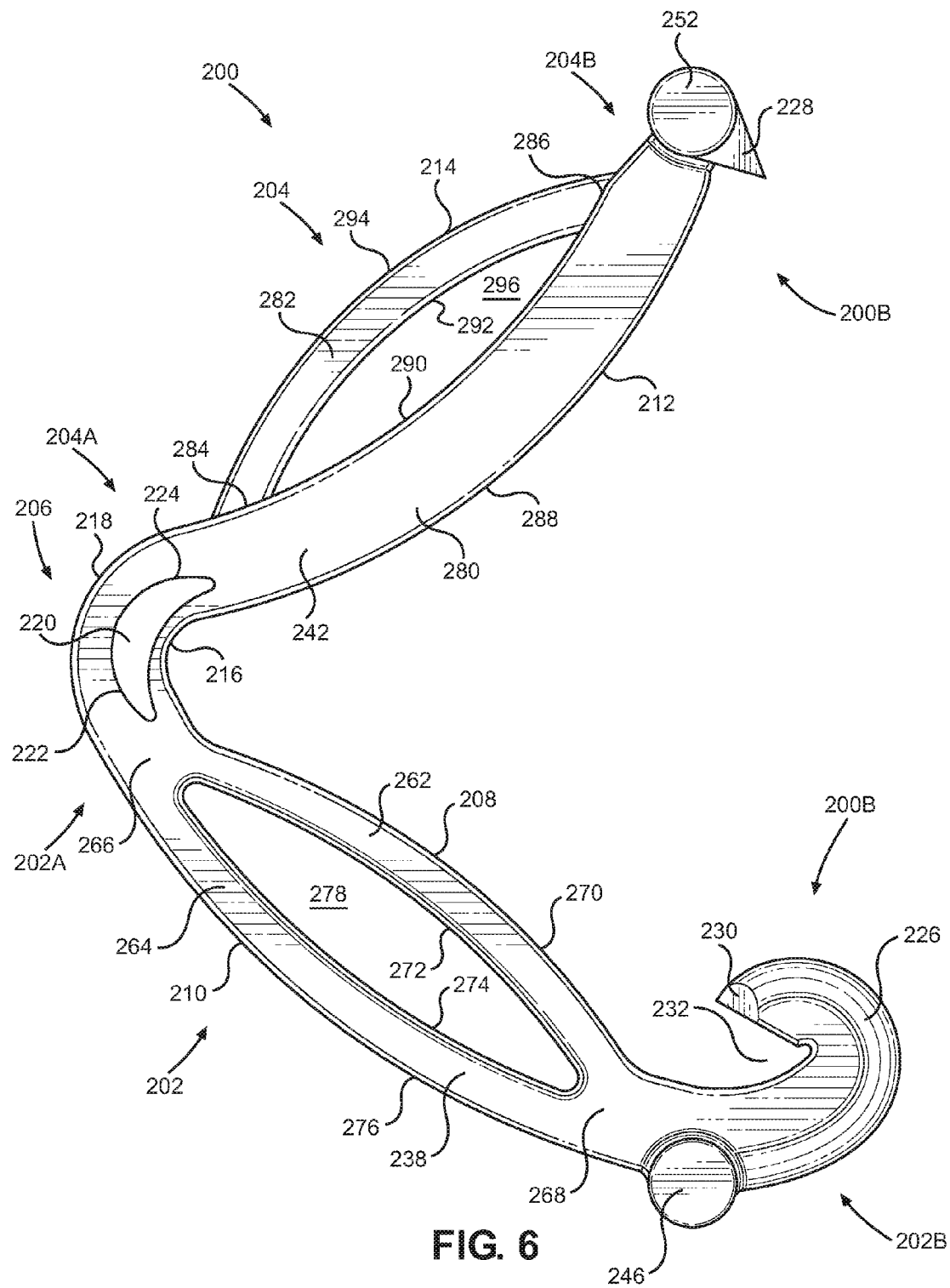
FIG. 6 illustrates a side view of a second exemplary embodiment of a surgical ligation clip of the present disclosure.
Figure 7:
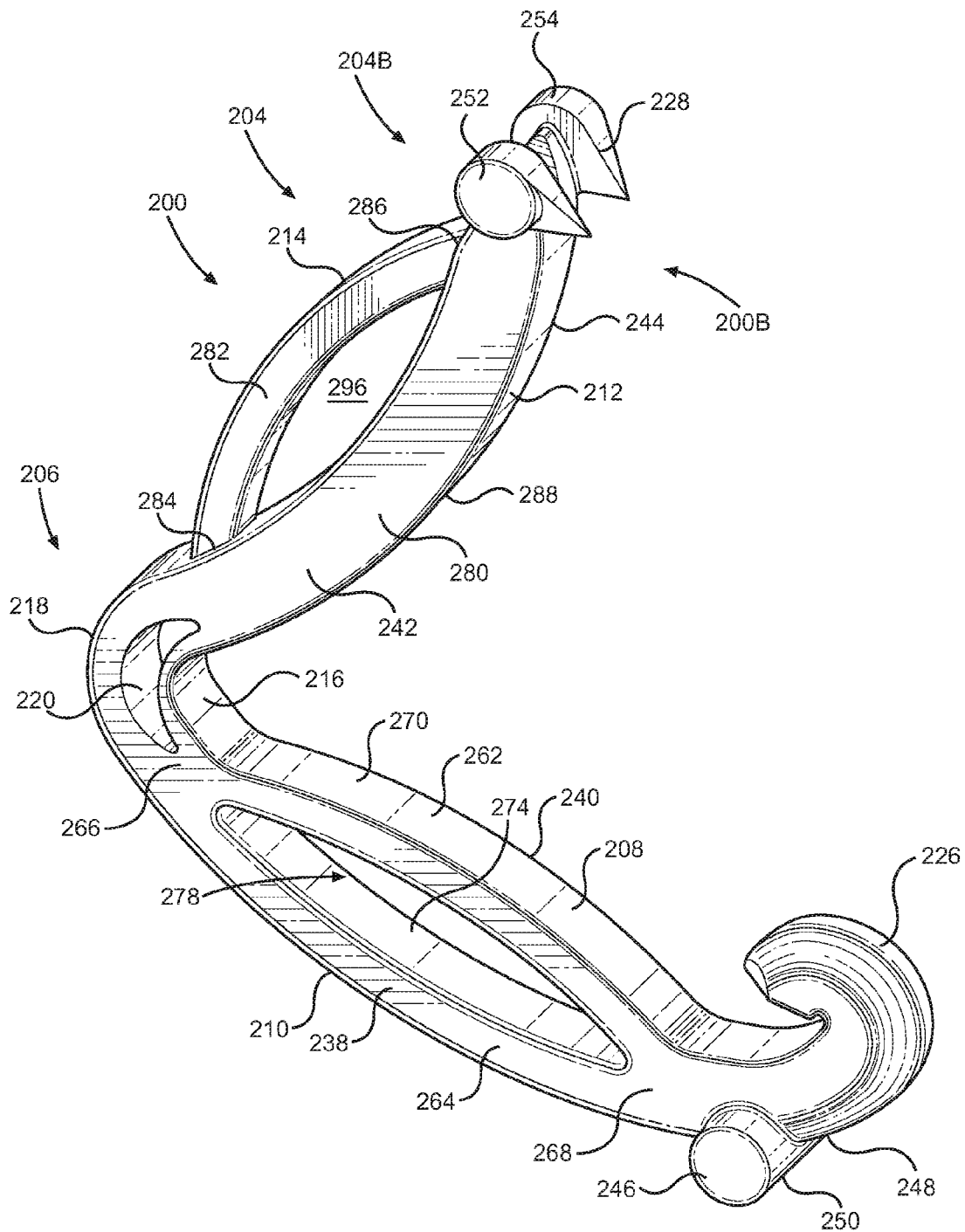
FIG. 7 illustrates a first perspective view of the second exemplary embodiment of the surgical ligation clip of FIG. 6.
Figure 8:
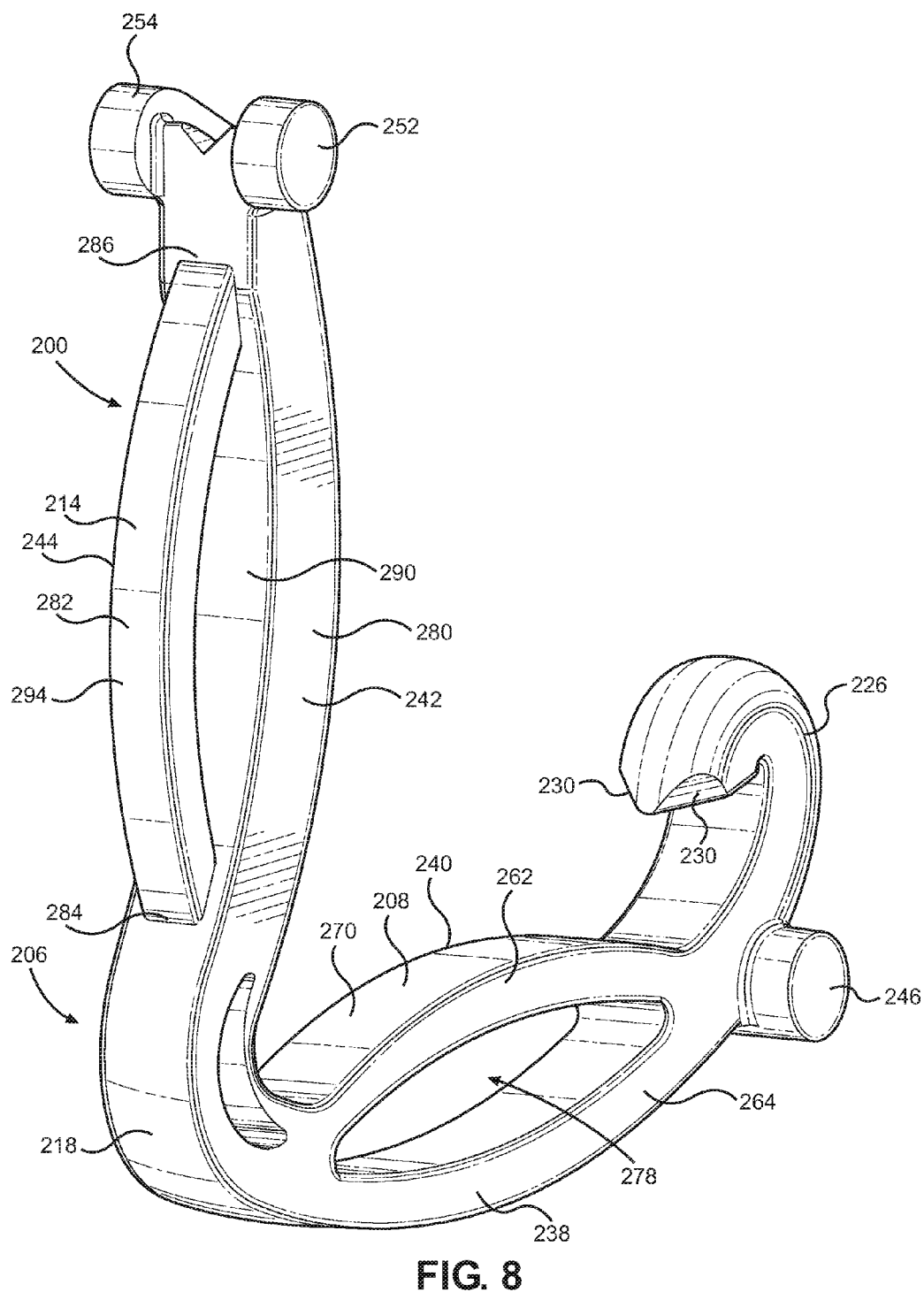
FIG. 8 illustrates a second perspective view of the second exemplary embodiment of the surgical ligation clip of FIGS. 6 and 7.

FIG. 6 is a side view of a second embodiment of a surgical ligation clip 200. FIGS. 7 and 8 show perspective views of clip 200.

Clip 200 may have a proximal end portion 200A and a distal end portion 200B. Clip 200 may further include a first leg member 202 having a proximal end portion 202A and distal end portion 202B, and a second leg member 204 having a proximal end portion 204A and distal end portion 204B. First and second leg members 202, 204 may include surfaces having curved portions. For example, first leg member 202 may include a first inner surface 208 and a first outer surface 210, and second leg member 204 may include a second inner surface 212 and a second outer surface 214. As illustrated in FIGS. 6-8, first inner surface 208 may include a convex portion, and second outer surface 210 may include a convex portion. The second inner surface 212 may include a convex portion, and the second outer surface 214 may include a convex portion.

First and second leg members 202, 204 may be joined at proximal end portions 202A, 204A by a hinge portion 206. Hinge portion 206 may be resilient and/or integral to clip 200. Clip 200 may also include a latching mechanism formed by latching elements on first and second leg members 202, 204. For example, first leg member 202 may transition to a curved, C-shaped hook section 226 at its distal end. Leg members 202, 204 may also include one or more bosses along their length to engage a clip applier. Although, clip 200 may include a first plurality of teeth (not shown) protruding on first inner surface 208, and a second plurality of teeth (not shown) protruding on second inner surface 212, for example, as depicted in FIGS. 1-3.

Second leg member 202 may include an inner portion 262 and an outer portion 264 joined at a first portion 266 and a second portion 268 of first leg member 202. Inner portion 262 may include a convex portion when viewed from inner side of first leg member 202, having an inner surface 270 that may be convex and an outer surface 272 that may be concave. Outer portion 264 may include a concave portion when viewed from inner side of first leg member 202, having an inner surface 274 that may be concave and an outer surface 276 that may be convex. It is contemplated that inner portion 262 and/or outer portion 264 may have a number of different curvatures. For example, inner portion 262 may include one or more concave, convex, and/or flat inner surfaces and one or more concave, convex, and/or flat outer surfaces. Outer portion 264 may include one or more concave, convex, and/or flat inner surfaces and one or more concave, convex, and/or flat outer surfaces.

Inner surface 270 of inner portion 262 may define at least a portion of first inner surface 208, and outer surface 276 of outer portion 264 may define at least a portion of first outer surface 210 of clip 200. For example, in some embodiments, inner portion 262 and outer portion 264 may extend greater than half of a length of first leg member 202 (e.g., defining greater than half of surfaces 208, 210). In some embodiments, inner portion 262 and outer portion 264 may extend greater than three-quarters of a longitudinal length first leg member 202 (e.g., defining greater than three-quarters of the length of surfaces 208, 210). Each of inner portion 262 and outer portion 264 may have a thickness less than a thickness of second leg member 204. For example, the thickness of each of inner portion 262 and/or outer portion 264 may be substantially half of the thickness of each of first leg member 202 and second leg member 204. The reduced thickness of inner portion 262 may provide the desired flexibility to conform to tissue compressed by clip 200. Inner portion 262, outer portion 164, and second leg member 204 may have substantially the same width in the transverse direction.

Inner portion 262 and outer portion 264 may be separated by at least one aperture or channel 278 extending longitudinally along the clip 200 to enable compression of first leg member 202. The channel 278 may extend between side surfaces 238, 240 of first leg member 202. For example, channel 278 may enable inner portion 262 to resiliently compress toward outer portion 264 and distribute load along the length of the tissue, while more effectively gripping and retaining the tissue within clip 200. In some embodiments, the channel 278 may extend in a longitudinal direction more than half a length of the first leg member 202. In some embodiments, the channel 278 may extend in a longitudinal direction greater than three-quarters of the length of the first leg member 202, as depicted in FIG. 6. The concavity of outer portion 264 may provide additional room for resilient deflection of inner portion 262, allowing clip 200 to ligate and properly distribute pressure to tissue of varying shapes, sizes, and/or stiffnesses. For example, inner portion 262 may provide continuous ligating pressure to tissue in a latched configuration, even as the tissue necrotizes and shrinks. In some embodiments, one or more ribs may extend between inner portion 262 and outer portion 264 to provide stiffness to first leg member 202 when desired.

Second leg member 204 may include an inner portion 280 and an outer portion 282 joined at a first portion 284 and a second portion 286 of first leg member 204. Inner portion 280 may include a convex portion When viewed from the inner side of second leg member 204, having an inner surface 288 that may be convex and an outer surface 290 that may be concave. Outer portion 282 may include a concave portion when viewed from the inner side of first leg member 204, having an inner surface 292 that may be concave and an outer surface 294 that may be convex. It is contemplated that inner portion 280 and/or outer portion 282 may have a number of different curvatures. For example, inner portion 280 may include one or more concave, convex, and/or flat inner surfaces and one or more concave, convex, and/or flat outer surfaces. Outer portion 282 may include one or more concave, convex, and/or flat inner surfaces and one or more concave, convex, and/or flat outer surfaces.

Convex inner surface 288 of inner portion 280 may define at least a portion of second inner surface 212, and convex outer surface 294 of outer portion 282 may define at least a portion of second outer surface 214 of clip 200. For example, in some embodiments, inner portion 280 and outer portion 282 may extend greater than half of a length of second leg member 204 (e.g., defining greater than half of surfaces 212, 214). In some embodiments, inner portion 280 and outer portion 282 may extend greater than three-quarters of the length of second leg member 204 (e.g, defining greater than three-quarters of the length of surfaces 212. 214). Each of inner portion 280 and outer portion 282 may have a reduced thickness to provide desired flexibility to conform to tissue compressed by clip 200. Inner portion 280 may have a greater width in the transverse direction than the outer portion 282.

Inner portion 280 and outer portion 282 may further define at least one aperture or channel 296 extending between side surfaces 242, 244 of second leg member 204 to enable compression of second leg member 204. For example, channel 296 may enable inner portion 280 to resiliently compress toward outer portion 282 and distribute load along the length of the tissue, while more effectively gripping and retaining the tissue within clip 200. In some embodiments, the channel 296 may extend in a longitudinal direction more than half a length of second leg member 202. In some embodiments, the channel 296 may extend in a longitudinal direction greater than three-quarters of the length of second leg member 204, as depicted in FIG. 6. The concavity of outer portion 282 may provide additional room for resilient deflection of inner portion 280, allowing clip 200 to ligate and properly distribute pressure to tissue of varying shapes, sizes, and/or stiffnesses. For example, inner portion 280 may provide continuous ligating pressure to tissue in a latched configuration, even as the tissue necrotizes and shrinks. In some embodiments, one or more ribs may extend between inner portion 280 and outer portion 282 to provide stiffness to second leg member 204 when desired.

As used herein, the term "longitudinal" is directed to the dimension which extends along the length of surgical clip 100, 200 and/or leg members 102, 104, 202, 204 from respective proximal end portions to respective distal end portions, as would be commonly understood by one of skill in the art. Furthermore, as used herein, the "transverse" direction is directed to any axis or direction which is orthogonal to the longitudinal lengths of surgical clip 100, 200 or leg members 102, 104, 202, 204, which would be normal to the plane of view, for example, in FIG. 1.

Clip 100, 200 may be made of any suitable size and may be applied to any number of tissues, such as blood vessels, lymph nodes, nerves, fallopian tubes, or cardiac tissue. Clip 100, 200 may be constructed from any suitable biocompatible material, such as certain metals and polymers. However, the present invention is particularly suitable for practice with polymeric clips. Thus, clip 100, 200 preferably comprises a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded or otherwise processed into like articles.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

| Parts List | |
|---|---|
| surgical ligation clip | 100 |
| proximal end portion | 100A |
| distal end portion | 100B |
| first leg member | 102 |
| proximal end portion | 102A |
| distal end portion | 102B |
| second leg member | 104 |
| proximal end portion | 104A |
| distal end portion | 104B |
| hinge portion | 106 |
| first inner surface | 108 |
| first outer surface | 110 |
| second inner surface | 112 |
| second outer surface | 114 |
| inner surface | 116 |
| outer surface | 118 |
| curved slot | 120 |
| opposite end | 122 |
| opposite end | 124 |
| hook section | 126 |
| tip section | 128 |
| transverse beveled surfaces | 130 |
| recess | 132 |
| first plurality of teeth | 134 |
| second plurality of teeth | 136 |
| side surfaces | 138 |
| side surfaces | 140 |
| side surfaces | 142 |
| side surfaces | 144 |
| boss | 146 |
| boss | 148 |
| bridge section | 150 |
| boss | 152 |
| boss | 154 |
| inner portion | 162 |
| deflect inner portion | 162 |
| outer portion | 164 |
| first portion | 166 |
| second portion | 168 |
| inner surface | 170 |
| outer surface | 172 |
| inner surface | 174 |
| outer surface | 176 |
| aperture | 178 |
| channel | 178 |
| surgical ligation clip | 200 |
| proximal end portion | 200A |
| distal end portion | 200B |
| first leg member | 202 |
| proximal end portion | 202A |
| distal end portion | 202B |
| second leg member | 204 |
| proximal end portion | 204A |
| distal end portion | 204B |
| hinge portion | 206 |
| first inner surface | 208 |
| first outer surface | 210 |
| second inner surface | 212 |
| second outer surface | 214 |
| inner surface | 216 |
| outer surface | 218 |
| curved slot | 220 |
| opposite end | 222 |
| opposite end | 224 |
| C-shaped hook section | 226 |
| tip section | 228 |
| transverse beveled surfaces | 230 |
| recess | 232 |
| side surface | 238 |
| side surface | 240 |
| side surface | 242 |
| side surface | 244 |
| boss | 246 |
| boss | 248 |
| bridge section | 250 |
| boss | 252 |
| boss | 254 |
| inner portion | 262 |
| outer portion | 264 |
| first portion | 266 |
| second portion | 268 |
| inner surface | 270 |
| outer surface | 272 |
| inner surface | 274 |
| outer surface | 276 |
| aperture | 278 |
| inner portion | 280 |
| outer portion | 282 |
| first portion | 284 |
| second portion | 286 |
| inner surface | 288 |
| outer surface | 290 |
| inner surface | 292 |
| outer surface | 294 |
| aperture | 296 |
| tissue | 500 |
| rigid tissue | 510 |
| compliant tissue | 520 |

What is claimed is:

1. A surgical clip configured to ligate a tissue, the surgical clip comprising:
    a first leg member having a proximal end portion, a distal end portion, a convex first inner surface, and a convex first outer surface, the first leg member including a first inner portion at least partially defining the first inner surface and a first outer portion at least partially defining the first outer surface, the first inner portion and the first outer portion being joined at first and second portions of the first leg member and separated by a first channel, and the first inner portion having a concave outer surface; and
    a second leg member having a proximal end portion, a distal end portion, a second inner surface, and a second outer surface, wherein the first and second leg members are movable relative to each other between an open configuration and a closed configuration, and the first and second inner surfaces are configured to ligate the tissue when in the closed configuration.

2. The surgical clip of claim 1, wherein the first inner portion is configured to be resiliently deflected in the closed configuration.

3. The surgical clip of claim 1, wherein the second inner surface includes a convex inner surface, and wherein the first and second inner surfaces are configured to pinch a proximal portion as the surgical clip is initially compressed.

4. The surgical clip of claim 1, wherein the first inner portion and the first outer portion are integral to the first leg member.

5. The surgical clip of claim 1, wherein the first inner portion has a width that is substantially equal to a width of the first outer portion.

6. The surgical clip of claim 1, wherein the first channel extends in a longitudinal direction for at least half of a length of the first leg member.

7. The surgical clip of claim 6, wherein the first channel extends in the longitudinal direction for greater than three-quarters of the length of the first leg member.

8. The surgical clip of claim 1, further comprising a hinge portion joining the proximal end portions of the first and second leg members.

9. The surgical clip of claim 8, wherein the hinge portion is integral to the first and second leg members.

10. The surgical clip of claim 1, further comprising:
   at least one first tooth positioned on the first inner surface; and
   at least one second tooth positioned on the second inner surface.

11. The surgical clip of claim 1, wherein the first and second leg members include latching elements configured to secure the surgical clip in the closed configuration.

12. The surgical clip of claim 1, wherein each of the first and second leg members includes at least one boss.

13. The surgical clip of claim 1, wherein the second leg member includes a second inner portion at least partially defining the second inner surface and a second outer portion at least partially defining the second outer surface, the second inner portion and the second outer portion being joined at first and second portions of the second leg member and separated by a second channel.

14. The surgical clip of claim 13, wherein the second inner portion includes a concave outer surface, and the second outer portion includes a concave inner surface.

15. The surgical clip of claim 1, wherein the first outer portion has a concave inner surface.

16. A surgical clip configured to ligate a tissue, the surgical clip comprising:
   a first leg member having a proximal end portion, a distal end portion, a convex first inner surface, and a convex first outer surface, wherein the first leg member includes a first inner portion at least partially defining the first inner surface and a first outer portion at least partially defining the first outer surface, and the first inner portion and the first outer portion are joined at first and second portions of the first leg member and separated by a first channel; and
   a second leg member having a proximal end portion, a distal end portion, a convex second inner surface, and a convex second outer surface, wherein the second leg member includes a second inner portion at least partially defining the second inner surface and a second outer portion at least partially defining the second outer surface, the second inner portion and the second outer portion being joined at first and second portions of the second leg member and separated by a second channel,
   wherein the first and second leg members are movable relative to each other between an open configuration and a closed configuration, and the first and second inner surfaces are configured to ligate the tissue when in the closed configuration.

17. A method of ligating a tissue with the surgical clip of claim 1, the method comprising:
   moving the first leg member relative to the second leg member from the open configuration toward the closed configuration;
   compressing at least a portion of the tissue between the first leg member and the second leg member by engaging the tissue with the convex first inner surface; and
   resiliently deflecting the first inner portion toward the first outer portion as the tissue is compressed.

18. The method of claim 17, wherein resiliently deflecting the first inner portion includes resiliently deflecting the first inner portion toward a concave inner surface of the first outer portion of the first leg member.

19. The method of claim 17, further comprising:
   retracting the tissue with the surgical clip after compressing the at least a portion of the tissue; and
   moving the surgical clip into the closed configuration after retracting the tissue with the surgical clip.

20. The method of claim 17, further comprising securing the surgical clip in the closed configuration with latching elements on the first and second leg members.

21. A surgical clip configured to ligate a tissue, the surgical clip comprising:
   a first leg member having a proximal end portion, a distal end portion, a convex first inner surface, and a convex first outer surface, the first leg member including a first inner portion at least partially defining the first inner surface and a first outer portion at least partially defining the first outer surface, the first inner portion and the first outer portion being joined at first and second portions of the first leg member and separated by a first channel, the first inner portion having a concave outer surface, and the first inner portion and the first outer portion are integrally formed; and
   a second leg member having a proximal end portion, a distal end portion, a second inner surface, and a second outer surface, wherein the first and second leg members are movable relative to each other between an open configuration and a closed configuration, the first and second inner surfaces are configured to ligate the tissue when in the closed configuration, and the first inner portion is configured to resiliently deflect toward the first outer portion in the closed configuration.

22. The surgical clip of claim 21, wherein the first inner portion has a width that is substantially equal to a width of the first outer portion.

23. The surgical clip of claim 21, wherein the first channel extends in a longitudinal direction for at least half of a length of the first leg member.

24. The surgical clip of claim 23, wherein the first channel extends in the longitudinal direction for greater than three-quarters of the length of the first leg member.

25. The surgical clip of claim 21, further comprising a hinge portion integrally joining the proximal end portions of the first and second leg members.

26. The surgical clip of claim 21, further comprising:
   at least one first tooth positioned on the first inner surface; and
   at least one second tooth positioned on the second inner surface.

27. The surgical clip of claim 21, wherein the first and second leg members include latching elements configured to secure the surgical clip in the closed configuration.

28. The surgical clip of claim 21, wherein each of the first and second leg members includes at least one boss.

29. The surgical clip of claim 21, wherein the first outer portion has a concave inner surface.

* * * * *